US012668566B2

(12) United States Patent
Long et al.

(10) Patent No.: US 12,668,566 B2
(45) Date of Patent: Jun. 30, 2026

(54) PREPARATION METHOD FOR SALICYLAMINE ACETATE

(71) Applicant: TSI Group Co., Ltd., Jiangsu (CN)

(72) Inventors: Ling Long, Shanghai (CN); Jianyi Ma, Shanghai (CN); Weiguo Liu, Shanghai (CN); Zhouya Liu, Shanghai (CN)

(73) Assignee: TSI Group Co., Ltd., Shanghai (CN)

( * ) Notice: Subject to any disclaimer, the term of this patent is extended or adjusted under 35 U.S.C. 154(b) by 773 days.

(21) Appl. No.: 17/613,834

(22) PCT Filed: May 21, 2020

(86) PCT No.: PCT/CN2020/091546
§ 371 (c)(1),
(2) Date: Jun. 21, 2022

(87) PCT Pub. No.: WO2020/238753
PCT Pub. Date: Dec. 3, 2020

(65) Prior Publication Data

US 2022/0315524 A1 Oct. 6, 2022

(30) Foreign Application Priority Data

May 24, 2019 (CN) ......................... 201910440439.9

(51) Int. Cl.
*C07C 213/02* (2006.01)
*C07C 51/41* (2006.01)

(52) U.S. Cl.
CPC .......... *C07C 213/02* (2013.01); *C07C 51/412* (2013.01)

(58) Field of Classification Search
CPC ... C07C 213/02; C07C 215/50; C07C 269/06; C07C 271/16; C07C 51/412; Y02P 20/55
See application file for complete search history.

(56) References Cited

U.S. PATENT DOCUMENTS 11,512,044 B2 * 11/2022 Long ...................... C07C 269/04
2007/0203214 A1 8/2007 Salvatore et al.
2021/0053907 A1 * 2/2021 Long ....................... C07C 53/10

FOREIGN PATENT DOCUMENTS

BR 112020010618 B1 11/2020
CN 102295594 * 12/2011
CN 102295594 B 12/2011
EP 3719002 A1 10/2020
JP H07330702 12/1995
WO 2019105324 A1 6/2019
WO WO2019/105324 * 6/2019

OTHER PUBLICATIONS

Mestichelli et al. (Concise Copper-Catalyzed Synthesis of Tricyclic Biaryl Ether-Linked Aza-Heterocyclic Ring Systems. Organic Letters, vol. 15, No. 21, pp. 5448-5451, Published Oct. 2013) (Year: 2013).*
Mestichelli et al. Supporting Information 276 pages (Year: 2013).*
Fuller et al. (Food and Chemical Toxicology, 121, pp. 541-548, Published 2018) (Year: 2018).*
Greene (Greene's Protective Groups in Organic Synthesis, fourth edition, pp. 696, 707, 725-735 and 748-756, Published 2007) (Year: 2007).*
CN 102295594 translation (Year: 2011).*
Zagol-Ikapitte et al. (Characterization of Scavengers of Gamma-Ketoaldehydes That Do Not Inhibit Prostaglandin Biosynthesis, Chem. Res. Toxicol., 23, pp. 240-250, Published 2010) (Year: 2010).*
Gopal Das, Braja , et al., "The direct reductive amination of electron-deficient amines with aldehydes: the unique reactivity of the Re2O7 catalyst", Chemical Communications, vol. 48, No. 66, Jan. 1, 2012.
Mestichelli, Paola , et al., "Concise Copper-Catalyzed Synthesis of Tricyclic Biaryl Ether-Linked Aza-Heterocyclic Ring Systems", Organic Letters, vol. 15, No. 21, Oct. 17, 2013.
Plattner, Jacob J, et al., "[(Aminomethyl)aryloxy]acetic Acid Esters. A New Class of High-Ceiling Diuretics. 3. Variation in the Bridge between the Aromatic Rings to Complete Mapping of the Receptor", Journal of Medicinal Chemistry, vol. 27, No. 12, Dec. 31, 1984, 1587-1596.
Zagol-Ikapitte, Irene , et al., "Characterization of Scavengers of y-Ketoaldeydes That Do Not Inhibit Prostaglandin Biosynthesis", Chemical Research in Toxicology, vol. 23, No. 1, Jan. 18, 2010.
"Cbz-Protected Amino Groups", < URL: https://www.organic-chemistry.org/protectivegroups/amino/cbz-amino.htm >.
Fuller, John C., et al., "In vitro safety pharmacology evaluation of 2-hydroxybenzylamine acetate", Food and Chemical Toxicology, vol. 121, 2018, 541-548.
Lee, Chanhyo , et al., "Colorimetric anion sensing by porphyrin-based anion receptors", Tetrahedron Letters, vol. 42, 2001, 8665-8668.

* cited by examiner

*Primary Examiner* — Amy C Bonaparte
*Assistant Examiner* — Blaine G Doletski
(74) *Attorney, Agent, or Firm* — Dentons Davis Brown

(57) ABSTRACT

A preparation method for salicylamine acetate, comprising preparing an amino-protected intermediate from salicylaldehyde, and reacting the intermediate with acetic acid to prepare an acetate.

9 Claims, 2 Drawing Sheets

| | |
|---|---|
| Compound ID | : A023 |
| Sample ID | : P12261-008-P8A |
| Vial# | : 69 |
| Injection Volume | : 1 |
| Filename | : D:\DATA\2018\1812\181212\P12261-008-P8A.lcd |
| Method Name | : D:\Method\10-80AB_6min_0.3.lcm |
| Instrument | : HPLC-N |
| Run time | : 2018-12-12 11:53:02 |

1 PDA Multi 1 / 220nm,4nm

Integration result

PeakTable

PDA Ch1 220nm

| Peak | Ret. Time | USP Width | Resolution | Height | Area | 100.000 |
|---|---|---|---|---|---|---|
| 1 | 0.416 | 0.074 | 0.000 | 192830 | 548442 | 100.000 |
| Total | | | | 192830 | 548442 | |

PREPARATION METHOD FOR SALICYLAMINE ACETATE

FIELD OF DISCLOSURE

The disclosure belongs to the field of chemical synthesis; and specifically relates to a method for preparing salicylamine acetate.

BACKGROUND OF DISCLOSURE

The compounds obtained by protecting salicylaldehyde with amino groups need to be hydrolyzed and deprotected by strong acid and then reacted with acetic acid to obtain salicylamine acetate. However, the commercial value of this method is limited. Therefore, there is an urgent need in the art to provide a method for preparing salicylamine acetate with low cost and excellent commercial effect.

SUMMARY OF DISCLOSURE

The purpose of the present disclosure is to provide a new method for preparing salicylamine acetate.

The present disclosure provides a method for preparing salicylamine acetate. The method includes the following steps:

(1) protecting a salicylaldehyde having a structure shown in Formula 1 with an amino group to obtain a compound having a structure shown in Formula 2; and (2) reacting the compound having the structure shown in Formula 2 with acetic acid to obtain salicylamine acetate;

1

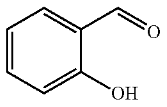

2

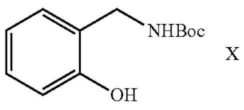

wherein, X=Cbz or Boc.

In another preferred embodiment, the reaction temperature of amino group protection in step (1) is 0-50° C.

In another preferred embodiment, the reaction time of amino group protection in step (1) is 3-18 hours.

In another preferred embodiment, the equivalent ratio of tert-butyl carbamate to salicylaldehyde in step (1) is 1.0-3.0:1.

In another preferred embodiment, the reaction solvent in step (1) is selected from the group consisting of tetrahydrofuran, 2-methyltetrahydrofuran, acetonitrile and 1,4-dioxane.

In another preferred embodiment, the temperature of reacting with acetic acid in step (2) is from 50° C. to the reflux temperature of acetic acid; and more preferably from 70° C. to the reflux temperature of acetic acid.

In another preferred embodiment, the time of reacting with acetic acid in step (2) is 5-70 hours; more preferably 5-60 hours.

In another preferred embodiment, in step (2), the ratio of the compound of Formula 2 to acetic acid is 1:0.1-20 (g/mL); preferably 1:1-15 (g/mL); and more preferably, 1:3-10 (g/mL).

In another preferred embodiment, the method includes the following steps:

(1) protecting the salicylaldehyde having the structure shown in Formula 1 with an amino group to obtain the compound having the structure shown in Formula 2;

(2) reacting the compound having the structure shown in Formula 2 with acetic acid, and lowering the temperature to room temperature after the reaction is complete, to obtain crude salicylamine acetate; and (3) mixing the obtained crude salicylamine acetate with an organic solvent and crystallizing to obtain pure salicylamine acetate; wherein the organic solvent is selected from the group consisting of ethyl acetate, isopropyl ether, absolute ethanol and methyl tert-butyl ether.

In another preferred embodiment, based on the amount of the compound of Formula 2, the amount of the organic solvent is 1-50 times; preferably 1-20 times; and more preferably 1-10 times.

Accordingly, the present disclosure provides a method for preparing salicylamine acetate with low cost and excellent commercial effect.

DETAILED DESCRIPTION

Figure 1:
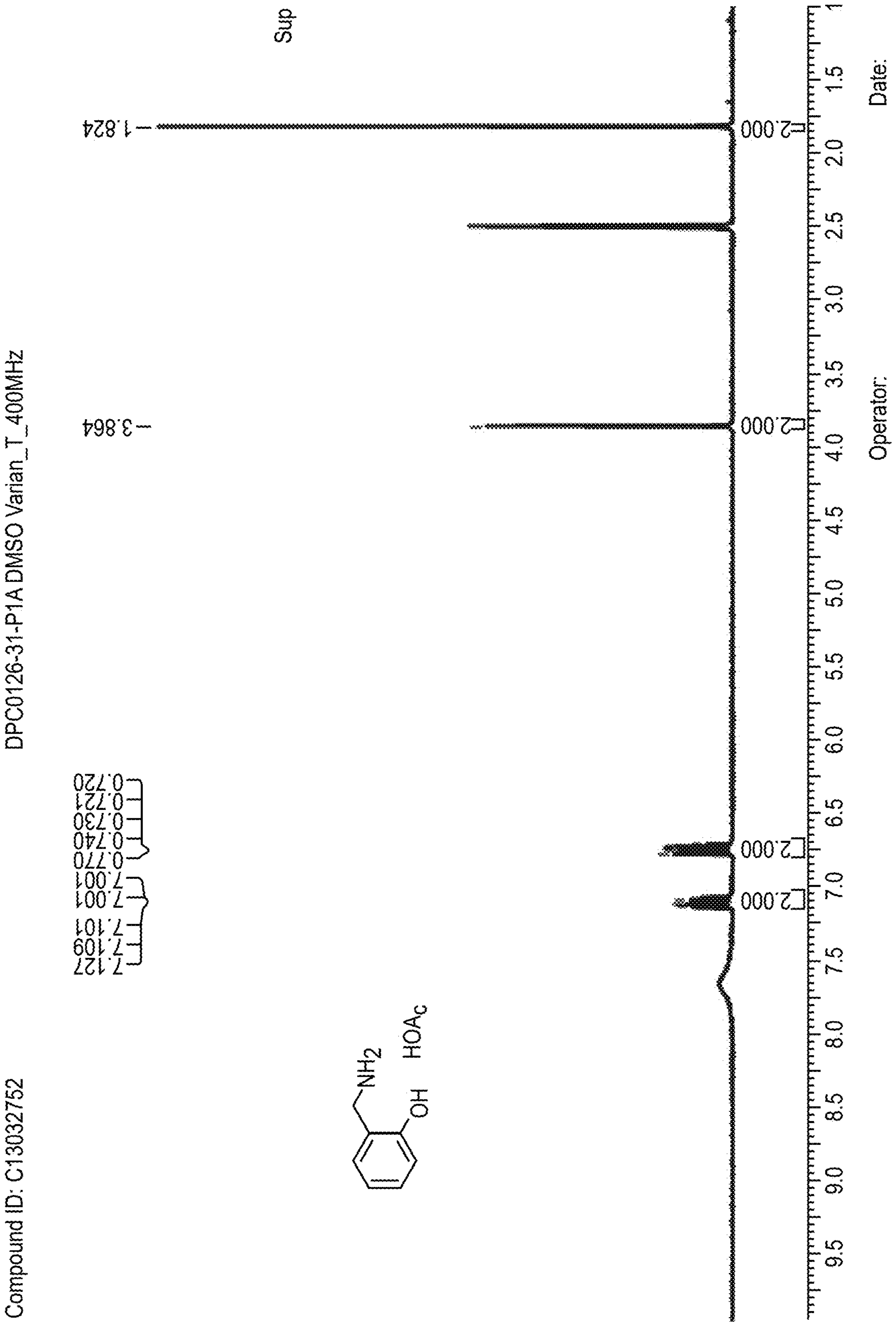
FIG. 1 shows a NMR spectrum of the salicylamine acetate obtained in the present disclosure.

Amino protecting groups are generally removed by strong acid hydrolysis, and weak acids such as acetic acid generally cannot achieve the removal. For example, a series of experiments for the following reactions are performed:

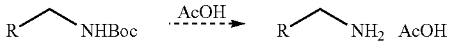

Table 1 shows the reaction conditions and results.

| | | | Results (17 h, %) | | |
|---|---|---|---|---|---|
| No. | Substrate (Structure and CAS number) | Reaction conditions | Material | Products | Other single impurity at highest amount |
| a | 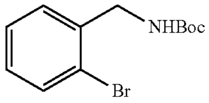 162356-90-3 | Adding the material (0.30 g) and glacial acetic acid (1.5 mL) into a reaction flask, and reacting for 17 hours by heating to 85-95° C. | 15.60 | 34.64 | 44.54 |
| b | 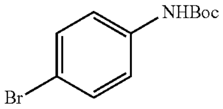 131818-17-2 | Adding the material (0.30 g) and glacial acetic acid (1.5 mL) into a reaction flask, and reacting for 17 hours by heating to 85-95° C. | 19.48 | 63.22 | 15.46 |
| c | 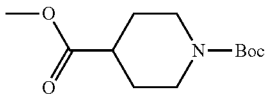 124443-68-1 | Adding the material (0.30 g) and glacial acetic acid (1.5 mL) into a reaction flask, and reacting for 24 hours by heating to 85-95° C. | 4.00 | 85.84 | 7.64 |
| Post-treatment | | After cooling to room temperature, adding 4.5 mL of methyl tert-butyl ether to each of the above three reaction liquids, and no solid precipitated. | | | |

The above reactions show that the effect of using acetic acid to deprotect the amino group is not good for the amino protecting groups on the benzene ring and other rigid structures. Although the material of different substrates can be detected by LCMS to show that the desired product can be formed, the amount of impurities produced is relatively large, especially for reactions a and b. In post-treatments of the three reactions, no solid was precipitated even when methyl tert-butyl ether was added. In order to obtain the desired product, the purification process will be very cumbersome.

On the contrary, the desired product of the present disclosure is salicylamine acetate. If acetic acid is used, the deprotection process and salt formation can be completed in one step. According to the prior arts, these reactions are either low in yield or complicated in post-treatment, which are not conducive to industrial production. The present inventor has conducted extensive and in-depth research and unexpectedly discovered that if some key factors are well controlled in the complex reaction environment, the amino-protected compound of salicylaldehyde can directly react with acetic acid to obtain salicylamine acetate, and high-purity products can be obtained by simple crystallization with organic solvents in subsequent treatment.

Said key factors include the ratio between the reaction substrate and acetic acid, the reaction temperature and time, and the choice of organic solvent for the subsequent crystallization process. On these basis, the present disclosure has been completed.

As used in the present disclosure, "the compound of Formula 1" or "the compound having the structure shown in Formula 1" can be used interchangeably, and both refer to salicylaldehyde. And other terms have similar meanings.

As used in the present disclosure, "room temperature" refers to 15-35° C., such as, but not limited to, 15-20° C., 15-25° C., 18-20° C., 15-30° C., 22-28° C., 24-30° C., 32-35° C. and so on.

Table 2 shows the compounds of the present disclosure:

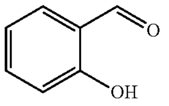

1

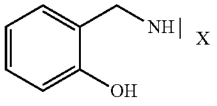

2 wherein, X = Cbz or Boc

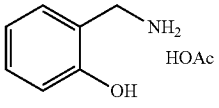

3

Specifically, the method for preparing salicylamine acetate having the structure shown in Formula 3 provided by the present disclosure includes the following steps:

Step 1, mixing the salicylaldehyde having the structure shown in Formula 1 with the amino protecting agent to obtain the compound having the structure shown in Formula 2;

Step 2, mixing and reacting the compound having the structure shown in Formula 2 with acetic acid, to obtain the salicylamine acetate of Formula 3.

In an embodiment of the present disclosure, the solvent contained in the mixture of salicylaldehyde having the structure shown in Formula 1 and amino protecting agent in step 1 is selected from the group consisting of tetrahydrofuran, 2-methyltetrahydrofuran, acetonitrile and 1,4-dioxane.

In an embodiment of the present disclosure, the mixture of salicylaldehyde having the structure shown in Formula 1 and amino protecting agent in step 1 further comprises triethylsilane.

In an embodiment of the present disclosure, the mixture of salicylaldehyde having the structure shown in Formula 1 and amino protecting agent in step 1 further comprises trifluoroacetic acid.

In an embodiment of the present disclosure, the mixing temperature in step 1 is 0-50° C., and preferably 10-50° C.

In an embodiment of the present disclosure, the mixing time in step 1 is 3-18 hours, and preferably 8-18 hours.

In an example of the present disclosure, in step 1, salicylaldehyde having the structure shown in Formula 1, amino protecting agent, triethylsilane and trifluoroacetic acid are mixed and kept at 0-50° C. (preferably 10-50° C.) for 3-18 hours (preferably 8-18 hours), to obtain the compound having the structure shown in Formula 2; wherein the amino protecting agent is selected from benzyl carbamate or tert-butyl carbamate; wherein the ratio between the amino protecting agent and salicylaldehyde is 1.0-3.0 equivalents: 1 equivalent; and wherein the ratio between triethylsilane and salicylaldehyde is 1.0-3.0 equivalents:1 equivalent.

In a preferred example of the present disclosure, the mixture is stirred while keeping the temperature.

In step 1, when tert-butyl carbamate is used, mixing is carried out in an organic solvent selected from the group consisting of tetrahydrofuran, 2-methyltetrahydrofuran, acetonitrile and 1,4-dioxane.

In a preferred example of the present disclosure, in step 1, a saturated inorganic alkali solution is used to quench the reaction to obtain the compound of Formula 2. Said inorganic alkali includes sodium bicarbonate, potassium bicarbonate, potassium carbonate, sodium carbonate, sodium hydroxide, lithium hydroxide, etc. The inorganic alkali solution can be used in any amount as long as the reaction can be quenched. Preferably, the inorganic alkali solution can make the mixture weakly alkaline, such as having a pH of 7-9, 7-8.5, 7-8, 7.5-8.5, 7.5-9 etc.

In another embodiment of the present disclosure, in step 2, the ratio of the compound of Formula 2 to acetic acid is 1:0.1-20 (g/mL); preferably 1:1-15 (g/mL); and more preferably, 1:3-10 (g/mL).

In an embodiment of the present disclosure, in step 2, the temperature for reacting with acetic acid is from 50° C. to the reflux temperature of acetic acid; preferably from 70° C. to the reflux temperature of acetic acid.

In an embodiment of the present disclosure, in step 2, the time for reacting with acetic acid is 5-70 hours, and preferably 5-60 hours.

Considering the reaction effect, in step 2, the reaction temperature is closely related to the reaction time. The higher the reaction temperature, the shorter the reaction time required, and vice versa. For example, but not limited to, at a reaction temperature lower than 70° C., the reaction can be carried out for more than 35 hours; and at a reaction temperature higher than 100° C., the reaction time can be less than 15 hours.

In a preferred embodiment of the present disclosure, an organic solvent can be added into the mixture containing acetic acid to crystallize, and salicylamine acetate having a relative high purity can be obtained after filtration. Based on the amount of the compound of Formula 2, the amount of organic solvent is 1-50 times; preferably 1-20 times; and more preferably 1-10 times. The organic solvent can be selected from the group consisting of ethyl acetate, isopropyl ether, absolute ethanol, and methyl tert-butyl ether (MTBE).

In a preferred embodiment of the present disclosure, the method for preparing salicylamine acetate having a structure shown in Formula 3 provided by the present disclosure includes the following steps:

Step 1, mixing the salicylaldehyde having the structure shown in Formula 1 with the amino protecting agent to obtain the compound having the structure shown in Formula 2;

Step 2, mixing and reacting the compound having the structure shown in Formula 2 with acetic acid, and lowering the temperature to room temperature after the reaction is completed, to obtain crude salicylamine acetate;

Step 3, mixing the crude salicylamine acetate with an organic solvent, and crystallizing to obtain salicylamine acetate having the structure shown in Formula 3 with a high purity.

In an embodiment of the present disclosure, the amount of organic solvent used in step 3 is 2-5 times (v/v), preferably 2-4 times of the amount of acetic acid used in step 2.

The features mentioned in the present disclosure or the features mentioned in the embodiments can be combined arbitrarily. All the features disclosed in the specification can be used in combination with any composition form, and each feature disclosed in the specification can be replaced by any alternative feature that can provide the same, equal or similar purpose. Therefore, unless otherwise specified, the disclosed features are only general examples of equal or similar features.

The main advantages of the present disclosure are:

1. The method for preparing salicylamine acetate provided by the present disclosure uses few raw materials, short route and low cost.
2. The method for preparing salicylamine acetate provided by the present disclosure is suitable for commercial application.
3. The salicylamine acetate obtained by the method of the present disclosure has a good appearance.

The present disclosure will be further explained below in conjunction with specific embodiments. It should be understood that these embodiments are only used to illustrate the present disclosure and not to limit the scope of the present disclosure. The experimental methods that do not indicate specific conditions in the following examples are usually in accordance with conventional conditions or in accordance with the conditions recommended by the manufacturer. Unless otherwise stated, all percentages, ratios, ratios, or parts are by weight. The unit of weight-volume percentage in the present disclosure is well-known to those skilled in the art, for example, refers to the weight of the solute in a 100 ml solution. Unless otherwise defined, all professional and scientific terms used in the disclosure have the same meaning as those familiar to those skilled in the art. In addition, any method and material similar or equivalent to the content described can be applied to the method of the present disclosure. The preferred implementation methods and materials described in the disclosure are for illustration purposes only.

In the following examples, the purity of the compound of Formula 3 is determined by high performance liquid chromatography. The stationary phase of high performance liquid chromatography is C18, the mobile phase is an aqueous solution of trifluoroacetic acid acetonitrile, and the detection wavelength is 220 nm. The purity is the percentage of the peak area of the compound of Formula 3 to the sum of the area of each peak.

EXAMPLE 1

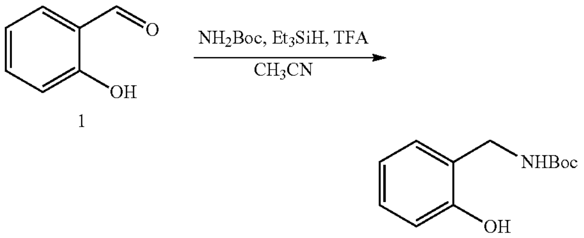

1

2

Acetonitrile (168.0 g) and the primarly material salicylaldehyde (70.4 g, 1.00 eq) were added into a 1 L reaction flask. Tert-butyl carbamate (74.0 g, 1.10 eq) and triethylsilane (79.0 g, 1.20 eq) were added into the 1 L reaction flask. Trifluoroacetic acid (65.4 g, 1.00 eq) was added dropwise to the reaction system under a temperature of 15° C.-40° C. After the addition was complete, the mixture was kept at 15-40° C. and stirred for 12-16 hours. Then, sampling was performed every 2-4 hours. When the HPLC detection showed that the content of the starting material was less than 5% or the change of two consecutive samples was less than 1%, 525 g of saturated sodium bicarbonate solution (490 g water+35 g sodium bicarbonate) was added to the system under the temperature of 15-30° C., to quench the reaction (the specific addition amount is subject to pH, pH=7-8). Then, the system was extracted twice with ethyl acetate, 252 g each time. The organic phases were combined and washed with 280 g of water and 336 g of saturated brine (252 g of water+84 g of sodium chloride). 100 g of anhydrous sodium sulfate was added to the organic phase, stirred and dried for 2-4 hours, centrifuged or suction filtered. The filter cake was rinsed with 63 g of ethyl acetate. The filter cake was temporarily stored, and the filtrate was combined for the next step (Example 2).

EXAMPLES 2-9

3

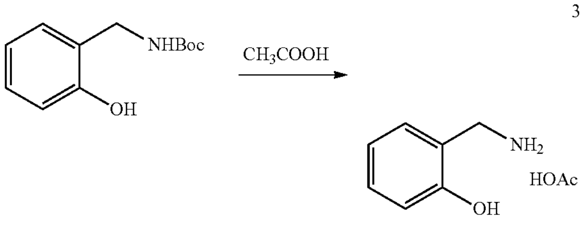

The spectrum data of the obtained product are:

$^1H$ NMR: DPC0126-31-P1A 400 MHz DMSO-$d_6$ $^1H$ NMR (400 MHz, DMSO-$d_6$) δ=7.14-7.04 (m, 2H), 6.78-6.68 (m, 2H), 3.85 (s, 2H), 1.82 (s, 3H)

MS 124.1: M+1, 107.1: M−16

The following is a description of the preparation process.

EXAMPLE 2

The compound of Formula 2 (2.0 g) and glacial acetic acid (2.0 mL) were added into a reaction flask. The mixture was stirred and reacted at 70-80° C. for 50-55 h. After the reaction was complete, the mixture was cooled to room temperature, and MTBE (6 mL) was added slowly to crystallize. The mixture was stirred at 10-20° C. for 0.5 h, filtered, and vacuum dried at 40° C. to constant weight. Weight: 0.75 g; yield: 45.73%; purity: 98.43%.

EXAMPLE 3

The compound of Formula 2 (2.0 g) and glacial acetic acid (8.0 mL) were added into a reaction flask. The mixture was stirred and reacted at 70-80° C. for 50-55 h. After the reaction was complete, the mixture was cooled to room temperature, and MTBE (24 mL) was added slowly to crystallize. The mixture was stirred at 10-20° C. for 0.5 h, filtered, and vacuum dried at 40° C. to constant weight. Weight: 0.81 g; yield: 49.39%; purity: 100.00%.

EXAMPLE 4

The compound of Formula 2 (2.0 g) and glacial acetic acid (12.0 mL) were added into a reaction flask. The mixture was stirred and reacted at 70-80° C. for 50-55 h. After the reaction was complete, the mixture was cooled to room temperature, and MTBE (36 mL) was added slowly to crystallize. The mixture was stirred at 10-20° C. for 0.5 h, filtered, and vacuum dried at 40° C. to constant weight. Weight: 0.79 g; yield: 48.17%; purity: 99.93%.

EXAMPLE 5

The compound of Formula 2 (2.0 g) and glacial acetic acid (20.0 mL) were added into a reaction flask. The mixture was stirred and reacted at 70-80° C. for 50-55 h. After the reaction was complete, the mixture was cooled to room temperature, and MTBE (60 mL) was added slowly to crystallize. The mixture was stirred at 10-20° C. for 0.5 h, filtered, and vacuum dried at 40° C. to constant weight. Weight: 0.95 g; yield: 57.93%; purity: 100.00.

EXAMPLE 6

The compound of Formula 2 (10.0 g) and glacial acetic acid (50.0 mL) were added into a reaction flask. The mixture was stirred and reacted at 60° C. for 48 h. After the reaction was complete, the mixture was cooled to room temperature, and MTBE (60 mL) was added slowly to crystallize. The mixture was stirred at 10-20° C. for 0.5 h, filtered, and vacuum dried at 40° C. to constant weight. Weight: 1.00 g; yield: 12.20%.

EXAMPLE 7

The compound of Formula 2 (10.0 g) and glacial acetic acid (50.0 mL) were added into a reaction flask. The mixture was stirred and reacted at 80-90° C. for 17-18 h. After the reaction was complete, the mixture was cooled to room temperature, and MTBE (150 mL) was added slowly to crystallize. The mixture was stirred at 10-20° C. for 0.5 h, filtered, and vacuum dried at 40° C. to constant weight. Weight: 4.20 g; yield: 51.22%; purity: 97.19%.

EXAMPLE 8

The compound of Formula 2 (10.0 g) and glacial acetic acid (50.0 mL) were added into a reaction flask. The mixture was stirred and reacted at 90-100° C. for 13-14 h. After the reaction was complete, the mixture was cooled to room temperature, and MTBE (150 mL) was added slowly to crystallize. The mixture was stirred at 10-20° C. for 0.5 h, filtered, and vacuum dried at 40° C. to constant weight. Weight: 5.11 g; yield: 62.32%; purity: 100.00%.

EXAMPLE 9

The compound of Formula 2 (10.0 g) and glacial acetic acid (50.0 mL) were added into a reaction flask. The mixture was stirred and reacted under reflux for 6-7 h. After the reaction was complete, the mixture was cooled to below 20° C., and MTBE (150 mL) was added slowly to crystallize. The mixture was stirred at 10-20° C. for 0.5 h, filtered, and vacuum dried at 40° C. to constant weight. Weight: 5.50 g; yield: 67.07%; purity: 98.64%.

EXAMPLE 10

The compound of Formula 2 and glacial acetic acid were added into a reaction flask. The mixture was stirred and reacted at 90-100° C. After the reaction was complete, the mixture was cooled to room temperature. The reaction liquid (120.6 g) was weighted and divided into 10 parts (each part theoretically contains 1.64 g of product). Solvent was added to crystallize.

1) One part (12.06 g) was taken and petroleum ether (36 mL) was added. No solid was precipitated (the system was layered). Then MTBE (36 mL) was added, and a large amount of solids precipitates. The mixture was filtered and dried at 40° C. to constant weight. Weight: 1.03 g; Yield: 62.80%;
2) One part (12.04 g) was taken and n-hexane (36 mL) was added. No solid was precipitated (the system was layered). Then MTBE (36 mL) was added, and a large amount of solids precipitates. The mixture was filtered and dried at 40° C. to constant weight. Weight: 1.07 g; Yield: 65.24%;
3) One part (12.05 g) was taken and cyclohexane (36 mL) was added. No solid was precipitated (the system was layered). Then MTBE (36 mL) was added, and a large amount of solids precipitates. The mixture was filtered and dried at 40° C. to constant weight. Weight: 1.02 g; Yield: 62.20%;
4) One part (12.06 g) was taken and n-heptane (36 mL) was added. No solid was precipitated (the system was layered). Then MTBE (36 mL) was added, and a large amount of solids precipitates. The mixture was filtered and dried at 40° C. to constant weight. Weight: 1.03 g; Yield: 62.80%;
5) One part (12.06 g) was taken and ethyl acetate (36 mL) was added. A large amount of solids precipitates. The mixture was filtered and dried at 40° C. to constant weight. Weight: 0.95 g; Yield: 57.93%;
6) One part (12.04 g) was taken and isopropyl ether (36 mL) was added. A large amount of solids precipitates. The mixture was filtered and dried at 40° C. to constant weight. Weight: 1.05 g; Yield: 64.02%;
7) One part (12.05 g) was taken and absolute ethanol (36 mL) was added. A large amount of solids precipitates. The mixture was filtered and dried at 40° C. to constant weight. Weight: 0.50 g; Yield: 30.49%;
8) One part (12.05 g) was taken and MTBE (36 mL) was added. A large amount of solids precipitates. The mixture was filtered and dried at 40° C. to constant weight. Weight: 1.00 g; Yield: 60.98%.

Figure 2:
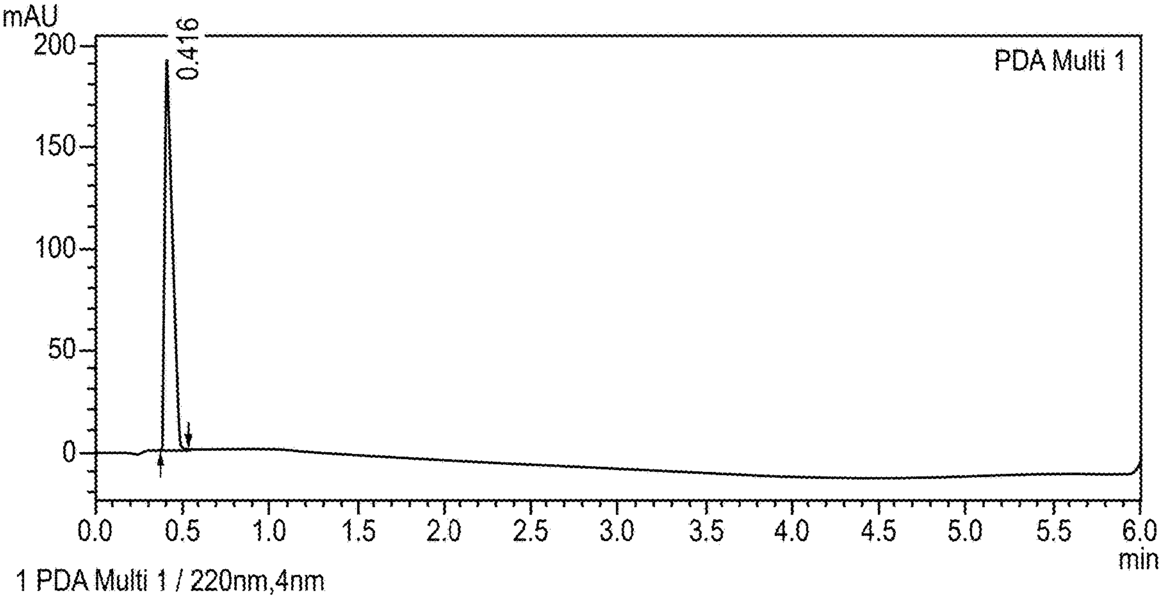
FIG. 2 shows a HPLC spectrum of the salicylamine acetate obtained in the present disclosure.

FIGS. 1 and 2 provided by the present disclosure showed that the present disclosure obtained salicylamine acetate with correct structure and high purity.

The above descriptions are only preferred embodiments of the present disclosure, and are not intended to limit the scope of the essential technical content of the present disclosure. The essential technical content of the present disclosure is broadly defined in the scope of the claims of the application, and any technical entity or method completed by others that is exactly the same as defined in the scope of the claims of the application, or an equivalent change, will be deemed to be covered by the scope of the claims.

We claim:

1. A method for preparing salicylamine acetate, wherein the method comprises the following steps:

(1) subjecting salicylaldehyde having a structure shown in Formula 1

1

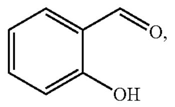

to amino protection to obtain a compound having a structure shown in Formula 2

2

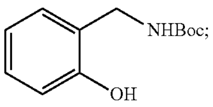

(2) reacting the compound having the structure shown in Formula 2 with acetic acid to obtain salicylamine acetate in one step, wherein the ratio of the compound of Formula 2 to acetic acid in step (2) is 1:1-20 (g/ml) and the temperature for reacting with acetic acid in step (2) is from 70° C. to the reflux temperature of acetic acid.

2. The method according to claim 1, wherein the reaction temperature of amino protection in step (1) is 0-50° C.

3. The method according to claim 1, wherein the reaction time of amino protection in step (1) is 3-18 hours.

4. The method according to claim 1, wherein the reaction solvent in step (1) is selected from the group consisting of tetrahydrofuran, 2-methyltetrahydrofuran, acetonitrile and 1,4-dioxane.

5. The method according to claim 1, wherein the ratio of the compound of Formula 2 to acetic acid in step (2) is 1:1-15 (g/mL).

6. The method according to claim 1, wherein the ratio of the compound of Formula 2 to acetic acid in step (2) is 1:3-10 (g/mL).

7. The method according to claim 1, wherein the method comprises the following steps:

(1) protecting the salicylaldehyde having the structure shown in Formula 1 with an amino group to obtain the compound having the structure shown in Formula 2;

(2) reacting the compound having the structure shown in Formula 2 with acetic acid, and lowering the temperature to room temperature after the reaction is complete, to obtain crude salicylamine acetate;

(3) mixing the obtained crude salicylamine acetate with an organic solvent and crystallizing to obtain pure salicylamine acetate; wherein the organic solvent is selected from the group consisting of ethyl acetate, isopropyl ether, absolute ethanol and methyl tert-butyl ether.

8. The method according to claim 1, wherein the time for reacting with acetic acid in step (2) is 5-70 hours.

9. The method according to claim 1, wherein the time for reacting with acetic acid in step (2) is 5-60 hours.

* * * * *